United States Patent [19]
Wakabayashi et al.

[11] Patent Number: 5,545,212
[45] Date of Patent: Aug. 13, 1996

[54] ARTIFICIAL BLOOD VESSEL

[75] Inventors: Sobei Wakabayashi; Tomoko Hashimukai, both of Fukui; Takeo Katakura; Yoshihito Takano, both of Kanagawa, all of Japan

[73] Assignees: Terumo Kabushiki Kaisha, Tokyo; Seiren Co., Ltd., Fukui, both of Japan

[21] Appl. No.: 345,323

[22] Filed: Nov. 21, 1994

Related U.S. Application Data

[63] Continuation of Ser. No. 992,103, Dec. 17, 1992, abandoned.

[30] Foreign Application Priority Data

Dec. 18, 1991 [JP] Japan ............................ 3-353569

[51] Int. Cl.⁶ .................................................. A61F 2/06
[52] U.S. Cl. ................................ 623/1; 623/11; 623/12
[58] Field of Search ................................... 623/1, 12, 13

[56] References Cited

U.S. PATENT DOCUMENTS

| | | | |
|---|---|---|---|
| 3,463,158 | 8/1969 | Schmitt et al. | 623/1 |
| 3,479,670 | 11/1969 | Medell | 623/1 |
| 4,649,920 | 3/1987 | Rhum | 128/335.5 |
| 4,834,755 | 5/1989 | Silvestrini et al. | 623/1 |
| 4,857,069 | 8/1989 | Kira . | |
| 4,921,495 | 5/1990 | Kira . | |
| 4,923,470 | 5/1990 | Dumican | 623/1 |
| 4,942,875 | 7/1990 | Hlavacek et al. | 623/1 |
| 4,954,127 | 9/1990 | Kira . | |

FOREIGN PATENT DOCUMENTS

| | | |
|---|---|---|
| 0122744 | 10/1984 | European Pat. Off. . |
| 0448840 | 10/1991 | European Pat. Off. . |
| 1577221 | 10/1980 | United Kingdom . |

OTHER PUBLICATIONS

Kinley, C. E. et al; *J. Cardiovas Surg.* 21, pp. 163–170 (1980).
Walden, R. et al, *Arch Surg.*, vol. 115, pp. 1166–119 (Oct. 1980).
Okuhn, S. P. et al, *J. Vascular Surg.* 36, pp. 35–45 (1989).
Tabata et al, *Jpn. J. Artificial Organs* 19(4), pp. 1427–1431 (1990).

*Primary Examiner*—Paul B. Prebilic
*Attorney, Agent, or Firm*—Burns, Doane, Swecker & Mathis

[57] ABSTRACT

An artificial blood vessel is formed of a tubular body of composite fibers. The composite fibers are composed of a polyethylene terephthalate and a polyester elastic body which are materials familiar with the tissue of an organism. The tubular body is produced by weaving, knitting or assembling processing, or the combined processing thereof, of the composite fibers.

20 Claims, 3 Drawing Sheets

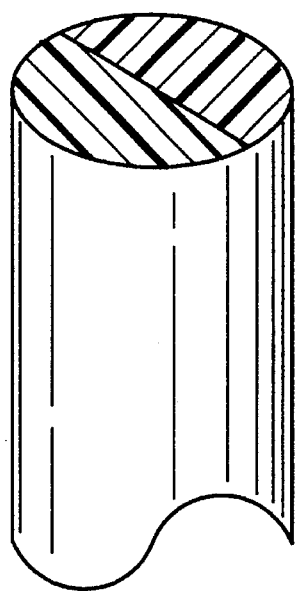 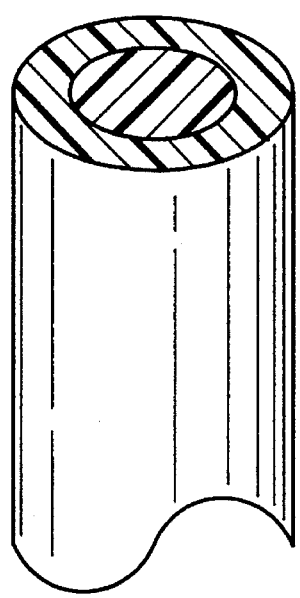 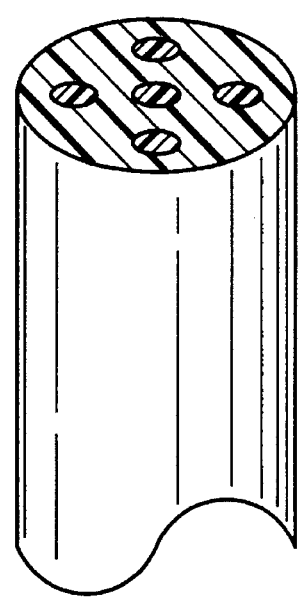
FIG. 1(a)  FIG. 1(b)  FIG. 1(c)
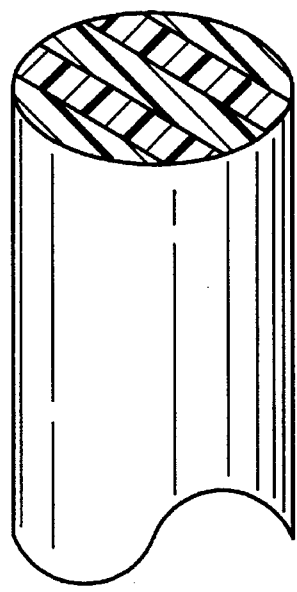 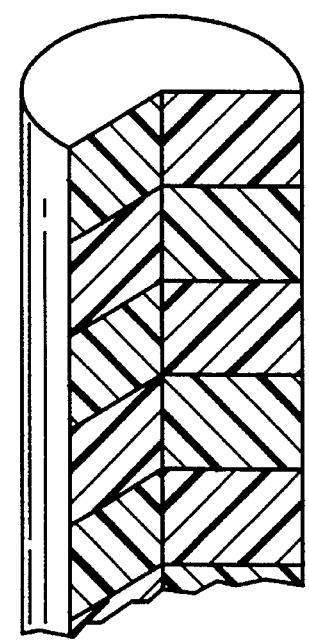
FIG. 1(d)  FIG. 1(e)

ARTIFICIAL BLOOD VESSEL

This application is a continuation of application Ser. No. 07/992,103, filed Dec. 17, 1992, now abandoned.

BACKGROUND OF THE INVENTION

1. Field of The Invention

The present invention relates generally to an artificial blood vessel composed of a tubular body made of fibers. More specifically, the invention relates to an artificial blood vessel which has properties approximating those of a vital blood vessel so that the tissue of endothelial cells can excellently adhere thereto.

2. Description of The Prior Art

In recent years, artificial blood vessels composed of a knitted or woven fabric made of polyesters, such as polyethylene terephthalate, and composed of an oriented polytetrafluoroethylene, have been developed and widely used. However, these artificial blood vessels are solid and do not have sufficient elastic properties so that their physical properties are unlike those of a vital blood vessel. Therefore, there is the disadvantage in that they are difficult to suture to a vital blood vessel. In particular, there is the disadvantage in that an artificial blood vessel made of a polyester cloth easily causes so-called kinking.

In order to eliminate the aforementioned disadvantage, crimp processing has been carried out to improve the bending and pressing resistances of an artificial blood vessel. In this case, there is another disadvantage that the inner surface (the bloodstream surface) of the artificial blood vessel is not smooth.

In recent years, small-diameter artificial blood vessels which can be used in the transplant into a peripheral arteria have been developed. Such a small-diameter artificial blood vessel must have a smooth and flat inner surface to have sufficient antithrombogenicity. Such a small-diameter artificial blood vessel is often made of a porous elastomer. However, when the aforementioned artificial blood vessel is made of the cloth, if crimping is carried out to improve the bending and pressing resistances of the artificial blood vessel and thereby prevent kinking, it is difficult for the artificial blood vessel to have the smooth and flat inner surface necessary for sufficient antithrombogenicity.

Furthermore, the aforementioned small-diameter artificial blood vessel preferably has a patency similar to the physical properties of a vital blood vessel to maintain the uniformity of the bloodstream. It has been reported that a difference between the physical properties (the elastic properties) of a vital blood vessel and an artificial blood vessel causes a disturbance of the bloodstream, and particularly that thrombus easily occurs at the anastomosed portion between blood vessels having different physical properties. Therefore, the raised intima influences the patency of the artificial blood vessel in long-term use (Kinley CE et al.; Compliance: a continuing problem with vascular grafts.; J Cardiovas Surg 21, 163–170 (1980)). It has been also reported that in order to solve the aforementioned problem, an artificial blood vessel must have physical properties (elastic properties) approximate to those of a vital blood vessel (Waden R. et al.; Marched Elastic Properties and Successful Arterial Grafting, Arch Surg vol. 115, 1166–1169 (October 1980)).

In order to solve the aforementioned problem, various artificial blood vessels made of elastic materials with physical properties similar to those of a vital blood vessel, have been developed. For example, such artificial blood vessels are composed of an elastic polymer of porous polyurethane (JP-A-60-182958 and JP-A- 60-188164), a multi-layer porous structure for preventing static electricity (JP-B-62-11861), and a laminate of non-woven porous sheets (JP-A-62-183757).

It has been recently reported that an artificial blood vessel made of polyurethane easily degrades after a long-term implantation (Tahara et al.; Clinical and experimental study on the insulation damage of polyurethane pacemaker leades: Jpn J Artif Organs 19(4), 1427–1431 (1990)). Therefore, it is preferable that an artificial blood vessel is not made of polyurethane. Furthermore, it is known that an artificial blood vessel is an artificial organ which is to be permanently operated in an organism, and water hammer stress due to strongly pulsing bloodstream is applied to the artificial blood vessel. Therefore, degradation of the material causes aneurysm, which must be prevented.

Furthermore, in the case of a small-diameter artificial blood vessel of a cloth, the aforementioned crimp processing should not be carried out in order to prevent an increase in thrombus.

SUMMARY OF THE INVENTION

It is therefore a principal object of the present invention to provide a novel artificial blood vessel.

It is another object of the present invention to provide an artificial blood vessel which has physical properties (elastic properties) similar to those of a vital blood vessel, and superior patency to allow cells and tissues to enter the vessel, and which can maintain a stable neoformation over a long term.

In order to accomplish the aforementioned and other objects, an artificial blood vessel, according to the present invention, is made of composite fibers.

According to one aspect of the present invention, an artificial blood vessel comprises a tubular body made of composite fibers composed of a polyethylene terephthalate and a polyester elastic body which are materials compatible with the tissue of an organism. The tubular body may have a woven or knitted structure, or a combined structure thereof, of the composite fibers.

BRIEF DESCRIPTION OF THE DRAWINGS

The present invention will be understood more fully from the detailed description given herebelow and from the accompanying drawings of the preferred embodiments of the invention. However, the drawings are not intended to imply any limitation of the invention to a specific embodiment, but are for explanation and understanding only.

In the drawings:

FIGS. 1(a) to 1(e) are cross-sectioned, perspective views of composite fibers usable for an artificial blood vessel, according to the present invention;

DESCRIPTION OF THE PREFERRED EMBODIMENT

Figure 2:
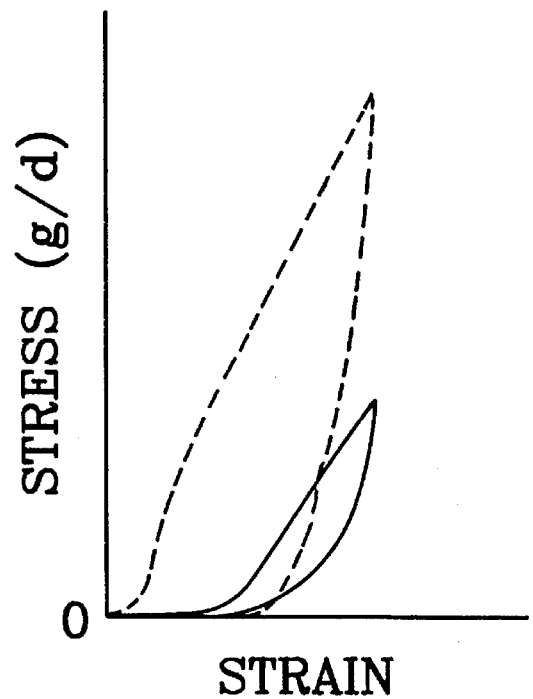
FIG. 2 is a graph showing an elongation recovery rate (strain) of the composite fiber used in Example 1 (expressed by the solid line: 60% constant elongation), and an elongation recovery rate (strain) of the usual fiber used in Comparative Example 1 (expressed by the broken line; 60% constant elongation)

The preferred embodiments of an artificial blood vessel, according to the present invention, will be described below.

An artificial blood vessel, according to the present invention, is made of composite fibers which may be obtained by compounding two kinds or more of polymers having different properties, in a single nozzle while separately controlling the discharge amounts of the respective polymers, and simultaneously spinning. The composite fiber of this type is called a "conjugated fiber".

In order to obtain an artificial blood vessel similar to a vital blood vessel, the composite fibers are generally used as the material thereof for the following purposes:

(a) for the purpose of applying a potential crimp property to the artificial blood vessel;

(b) for the purpose of improving the physical properties of the fiber, such as flexural rigidity, tensile strength and elastic recoverability;

(c) for the purpose of fibril formation or the formation of extra fine fibers, using the peeling between the components of the composite fiber;

(d) for the purpose of forming extra fine fibers by dissolving and removing one component using the difference of solubilities in a solvent between the components of the composite fiber;

(e) for the purpose of heat adhesion between the fibers by heat-processing using the difference between the melting points of the polymer components of the composite fiber: or (f) for the purpose of varying the hygroscopic property, feel, and wear and abrasion resistance, by varying the surface structure.

According to the present invention, the composite fiber is used for the aforementioned purpose (b), particularly for the purpose of improving elastic recoverability. If necessary, after the formation of the composite fibers, the potential crimp property in the aforementioned purpose (a) is further preferably applied to the formed composite fibers to form an artificial blood vessel having a stable tubular structure.

According to the present invention, an elastic material is used as one component of the composite fiber to improve the elastic recoverability. Specifically, the composite fiber has an elongation rate of not less than 2%, preferably not less than 5%, to have an elongation elastic recovery rate of 90%.

FIGS. 1(a) to 1(e) show various examples of composite fibers made of two or more components, in use for an artificial blood vessel, according to the present invention. FIG. 1(a) shows a conjugated type in which two components are connected so as to face each other. FIG. 1(b) shows a single core type in which one component serves as a core, and another component surrounds the core. FIG. 1(c) shows a multiple core type in which a plurality of cores are formed of one component, and another component surrounds all or a great part of these cores. FIG. 1(d) shows a multi-layer conjugated type in which two components are alternately connected to form multiple layers. FIG. 1(e) shows a longitudinally-directional composite type in which the polymers serving as the components of the composite fiber are connected alternately in the axial direction of the fiber to form a lamination of multiple layers. Although all the aforementioned various composite types of composite fibers can be used for an artificial blood vessel, according to the present invention, the composite fiber of the conjugated type shown in FIG. 1(a) is particularly preferable in view of the elastic property, the elastic recovery and the crimp property necessary for an artificial blood vessel.

According to the present invention, the composite fibers are preferably polyester fibers having a superior stability in an organism, which polyester fibers may comprise a polyethylene terephthalate and a polyester elastic body. The polyester elastic body may include a polybutylene terephthalate, a polyester-polyether block copolymer, and a polyester-polyester copolymer. The elastic body of the polyester-polyether block copolymer may comprise a hard segment of an aromatic polyester, such as a polyethylene terephthalate, a polyethylene terephthalate/isophthalate and a poly(1,4-cyclohexane dimethylene terephthalate), and a soft segment of an aliphatic polyether, such as a polyethylene glycol. Specifically, it may include, for example, Pelprene-S-type (Trademark; commercially available polyester-polyester type copolymer from Toyo Boseki Co., Ltd.) and Arnitel E,P (Trademark; commercially available polyester-polyester type copolymer from Akzo Co, Ltd.). The elastic body of the polyester-polyester copolymer may comprise a hard segment of an aromatic polyester, such as a polyethylene terephthalate, a polyethylene terephthalate/isophthalate and a poly(1,4-cyclohexane dimethylene terephthalate), and a soft segment of an aliphatic polyester, such as ethylene sebacate. Specifically, it may include Pelprene-P-type (Trademark; commercially available from Toyo Boseki Co., Ltd.). However, other elastic bodies may be used in an artificial blood vessel, according to the present invention.

The compositional ratio of the polyethylene terephthalate and the polyester elastic body may be optionally selected, and is preferably in the range of 20:80–80:20 by weight ratio. When the rate of the polyethylene terephthalate is too high, although the form stability is good, the elastic properties are spoiled. In addition, when both are unbalanced, the potential crimp property may be spoiled.

Furthermore, it is preferable to carry out a process for subliming the composite fibers to enhance the compatibility thereof in an organism. For example, the subliming process may be any one of well-known processes, such as (1) twisting-fixing by heat-untwisting method, (2) a temporary twisting method, (3) a pushing method, (4) an abrasion method, (5) an air injecting method, and (6) a forming method.

The thickness of the composite fiber, according to the present invention, may be in the range of 10 to 100 denier, preferably 20 to 50 denier, further preferably about 30 denier. It is not preferable that the thickness of the composite fiber be greater than 100 denier, since the elastic properties of the composite fiber reduces remarkably. On the other hand, when the thickness of the composite fiber is less than 10 denier, the composite fiber has high elasticity. However, such a thickness is not preferable, since the strength thereof is insufficient.

According to the present invention, the composite fibers thus obtained are woven or knitted, or processed by a combination of two or more such processes, to produce an artificial blood vessel made of a tubular cloth. Although a method for producing the tubular body may include a warp knitting work, a weft knitting work, a three-axis knitting work, a hollow weave and a braided rope, it should be limited to these methods.

The artificial blood vessel thus obtained preferably has innumerable fine crimp structures on the inside and outside surfaces, and an expansion property approximating that of a vital blood vessel. Such fine crimp structures may be obtained by, for example, air-jet confounding of the composite fibers prior to the weaving, knitting or assembling process of the fibers. The artificial blood vessel which has such fine crimp structures, has an expansion property in which when internal pressure of 150 mmHg is applied thereto, the extension percentage in the radial direction is in the range of 2 to 15%, preferably 5 to 15%, and the extension percentage in the longitudinal direction is in the range of 2 to 20%, preferably 5 to 15%. When the artificial blood vessel has the aforementioned extension percentages, the dependency on the pulsation of a vital blood vessel can be improved to provide a superior antithrombogenisity.

The inside diameter of the artificial blood vessel of the present invention may be optionally selected in a wide range of about 3 to 30mm in accordance with the site or the kind used. Particularly, if the inside diameter is a small diameter in the range of about 3 to 6 mm, the artificial blood vessel may have a very good patency. Furthermore, the wall thickness of the artificial blood vessel is necessarily determined on the basis of the inside diameter of the used composite fiber, and the processing method used, such as the weaving, knitting or assembling processing. The wall thickness is usually in the range of 0.4 to 0.5 mm.

Although the water permeability amount of an artificial blood vessel, according to the present invention, should not be limited to a specific value. it is preferably in the range of about 500 to 4000 cc/min./cm$^2$–120 mmHg, further preferably about 500 to 3000 cc/min./cm$^2$ –120 mmHg.

The artificial blood vessel of the present invention may be directly put into a human body after a sterilization treatment, so that cells and tissues may adhere when in the human body. Alternatively, cells of a blood vessel wall which was previously collected aseptically in vitro from a vital blood vessel in a host may be disseminated after sterilization, the surface of the blood vessel wall may be restructured in view of functional and Structural aspects so as to imitate a vital blood vessel, and then, the obtained artificial blood vessel may be transplanted. Furthermore, prior to use if necessary, well-known surface treatments, such as a heparin treatment for providing antithrombogenisity to the surface, may be carried out.

If necessary, a spiral or ring reinforcement made of a polyolefin resin may be applied so as to extend along the peripheral surface of the artificial blood vessel. By this reinforcement, it is unnecessary to carry out the crimp processing of the artificial blood vessel made of a cloth, which has been previously necessary for sites such as elbows and knees, where the cloth is frequently bent, and it is possible to reinforce the inner surface (the bloodstream surface) of the artificial blood vessel while maintaining the smooth and flat surface thereof.

The advantages of the present invention will be more fully understood by the following examples.

EXAMPLE 1

A polyethylene terephthalate was used as one component of a composite fiber, and a polyester elastic body of a polybutylene terephthalate was used as another component thereof. These components were separately fused by means of an extruder, and thereafter, introduced into a nozzle block set at 290° C. Using a known nozzle for conjugated type composite fibers, which nozzle was 0.5 mm in diameter and had 24 holes, fibers were rolled around reels at an extruding rate of 1000 m/min. at a rate of 20 g/min. per nozzle. The compositional ratio of the polyethylene terephthalate and the polybutylene terephthalate was 50:50 by weight ratio.

The orientation of the fibers thus obtained was carried out between a hot plate at 80° C. and a hot plate at 120° C., at a draw ratio of 1.8 times. The subliming process of the fibers was carried out at 200° C. at a number of twist of 2500 T/M in a known manner. The thickness of the composite fiber thus obtained was 50 denier. It was found that this fiber had superior elastic properties. The elastic recovery rate thereof is shown by the solid line in FIG. 2.

Using the composite fibers thus obtained, a tubular cloth was produced by means of a 30-gauge double raschel machine. The knitting work was a reverse-half knitting work which is one of a warp knitting work.

Then, the tubular cloth was turned inside out, and put into a bath containing 2 g/liter soda ash, 2 g/liter sodium tripolyphosphate, and 2 g/liter nonionic surface active agent. In this bath, the refinery processing of the tubular cloth was carried out at 90° C. for 20 minutes, to remove impurities and produce crimps. After the tubular cloth was washed with water and dried, the crimp processing thereof was carried out to obtain an artificial blood vessel having an inside diameter of 5 mm. The knitting density of the obtained artificial blood vessel was 70 loops/inch by 50 loops/inch, and the coefficient of water permeability thereof was 3000 cc/min./cm$^2$–120 mmHg.

Figure 3:
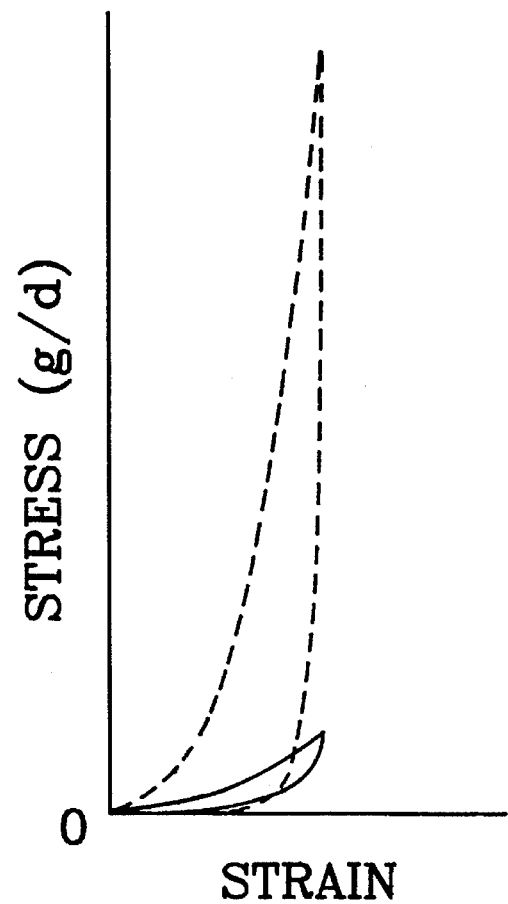
FIG. 3 is a graph showing an elongation recovery rate (strain) of the tubular artificial blood vessel produced in Example 1 (expressed by the solid line=60% constant elongation), and an elongation recovery rate (strain) of the tubular artificial blood vessel produced in Comparative Experiment 1 (expressed by the broken line; 60% constant elongation)

The elastic recovery rate of the obtained tubular artificial blood vessel is shown by the solid line in FIG. 3. It was found from FIG. 3 that this artificial blood vessel had flexibility and elasticity similar to those of a vital blood vessel. When internal pressure of 150 mmHg is applied to the obtained artificial blood vessel, the elongation percentage in the radial direction was 11%, and the elongation percentage in the longitudinal direction was 13%. Furthermore, it was found that the obtained artificial blood vessel had a great number of fine crimps on the inside and outside surfaces thereof, and a stable tissue structure which was difficult to loosen.

COMPARATIVE EXAMPLE 1

Using usual polyester yarns 75d/48f, a tubular cloth was produced by means of a 30-gauge double raschel machine. The knitting work was a reverse-half knitting which is one of a warp knitting work. The elastic recovery rate of the usual polyester yarns used in this Comparative Example is shown by the broken line in FIG. 2.

Then, the tubular cloth was turned inside out, and the refinery processing and the crimp processing were carried out to produce an artificial blood vessel having an inside diameter of 5 mm. The knitting density of the artificial blood vessel thus obtained was 65 loops/inch by 45 loops/inch, and the coefficient of water permeability thereof was 3500 cc/min./cm$^2$–110 mmHg.

The elastic recovery rate of this tubular artificial blood vessel is shown by the broken line in FIG. 3. It was found from FIG. 3 that the artificial blood vessel obtained in this Comparative Example had an elastic recovery property much smaller than that of Example 1, and did not have flexibility and elasticity similar to those of a vital blood vessel. Furthermore, when internal pressure of 150 mmHg is applied to the artificial blood vessel, the elongation percentage in the radial direction was 0%, and the elongation percentage in the longitudinal direction was 1%.

EXAMPLE 2

A spiral made of a polypropylene resin (0.5 mm in diameter, 2 mm in pitch, and 13cm in length) to which a contrast medium (bismuth oxide) was previously added, was molded. This spiral was wound onto the artificial blood vessel having an inside diameter of 5 mm (13 cm in length) produced in a similar manner to Example 1 except for the crimp processing, and set by heat to produce a spiral-reinforced artificial blood vessel. Although no crimp processing was carried out, this artificial blood vessel did not suffer from kinking due to bending, nor deformation due to the elasticity of the material.

Figure 4:
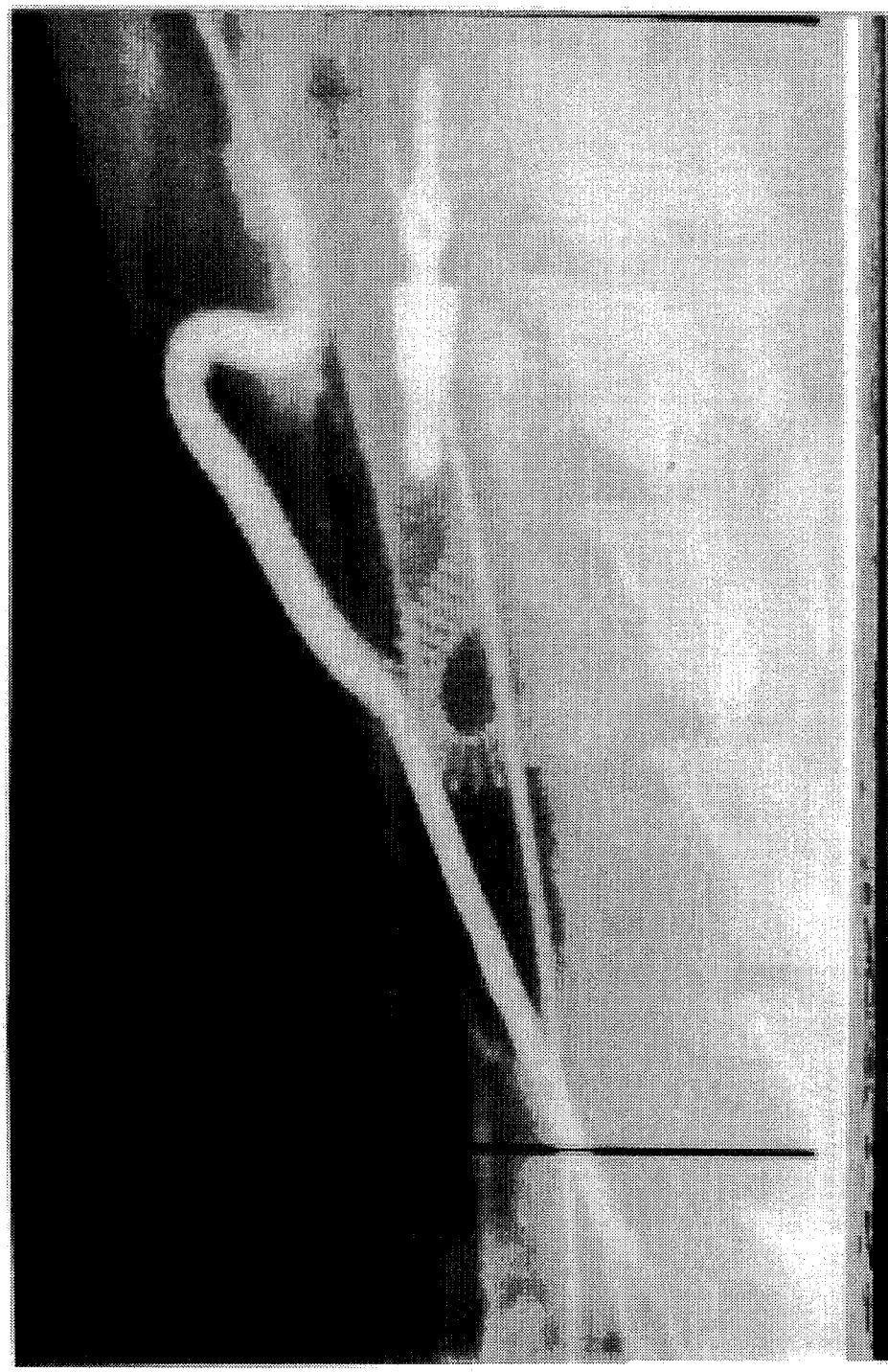
FIG. 4 is a X-ray contrast photograph showing the patency of an artificial blood vessel of the present invention after 3 months post-transplant into a mongrel dog (20kg in weight).

This spiral-reinforced artificial blood vessel was sterilized with ethylene oxide gas, and then, transplanted into the carotid artery of a mongrel dog of 20 kg in weight. Prior to transplant, the preclotting of the artificial blood vessel was carried out using blood from a dog. In the suturing processing at the transplant, a needle was inserted smoothly into the artificial blood vessel. After 3 months post-transplant, the patency of the transplanted blood vessel was examined by means of X-ray contrast, and thereafter, the sample was taken out- From a X-ray contrast photograph (FIG. 4), it was found that a smooth bloodstream was obtained without constriction at the anastomosed portion. It was also found that there was no expansion of the blood vessel, the irruption of cell components into the blood vessel wall was observed, and good curing was confirmed.

COMPARATIVE EXAMPLE 2

The artificial blood vessel having an inside diameter of 5mm (5cm in length) produced in Comparative Example 1 was transplanted into the carotid artery of a mongrel dog of 20kg in weight after preclotting in a similar manner to Example 2. After 1 month post-transplant, it was take out. Thrombus locally adhered to the wall of the artificial blood vessel was observed, and it was found that organization was not fully carried out. Furthermore, the intima at the anastomosed portion was slightly raised, so that there was danger of the blocking during long-term use after transplant.

What is claimed is:

1. An artificial blood vessel comprising a tubular body made of composite fibers composed of a polyethylene terephthalate and a polyester elastic body, said composite fiber being a conjugated fiber in which at least two components are alternately fused in the longitudinal direction with each component forming a layer and wherein said respective components form a part of the outer surface along said longitudinal direction of said fiber, wherein said polyethylene terephthalate and said polyester elastic body are compatible with the tissue of an organism.

2. An artificial blood vessel according to claim 1, wherein said tubular body has a woven, knitted or a combined knitted and woven structure comprised of said composite fibers.

3. An artificial blood vessel according to claim 1, wherein said polyester elastic body is selected from the group consisting of a polybutylene terephthalate, a polyester-polyether block copolymer, and a polyester-polyester copolymer.

4. An artificial blood vessel according to claim 3, wherein said polyester-polyether block copolymer comprises a hard segment of an aromatic polyester, and a soft segment of an aliphatic polyether.

5. An artificial blood vessel according to claim 4, wherein said aromatic polyester is selected from the group consisting of a polyethylene terephthalate, a copolymer consisting of polyethylene terephthalate and polyethylene and isophthalate and a poly(1,4-cyclohexane dimethylene terephthalate).

6. An artificial blood vessel according to claim 4, wherein said aromatic polyester is a polyethylene glycol.

7. An artificial blood vessel according to claim 3, wherein said polyester-polyester copolymer comprises a hard segment of an aromatic polyester, and a soft segment of an aliphatic polyether.

8. An artificial blood vessel according to claim 7, wherein said aromatic polyester is selected from the group consisting of a polyethylene terephthalate, a copolymer consisting of polyethylene terephthalate and polyethylene isophthalate and a poly(1,4-cyclohexane dimethylene terephthalate).

9. An artificial blood vessel according to claim 7, wherein said aromatic polyester is a polyethylene glycol.

10. An artificial blood vessel according to claim 2, wherein said polyester elastic body is selected from the group consisting of a polybutylene terephthalate, a polyester-polyether block copolymer, and a polyester-polyester copolymer.

11. An artificial blood vessel according to claim 10, wherein said polyester-polyether block copolymer comprises a hard segment of an aromatic polyester, and a soft segment of an aliphatic polyether.

12. An artificial blood vessel according to claim 11, wherein said aromatic polyester is selected from the group consisting of a polyethylene terephthalate, a a copolymer consisting of polyethylene terephthalate and polyethylene isophthalate and a poly(1,4-cyclohexane dimethylene terephthalate).

13. An artificial blood vessel according to claim 11, wherein said aromatic polyester is a polyethylene glycol.

14. An artificial blood vessel according to claim 10, wherein said polyester-polyester copolymer comprises a hard segment of an aromatic polyester, and a soft segment of an aliphatic polyether.

15. An artificial blood vessel according to claim 14, wherein said aromatic polyester is selected from the group consisting of a polyethylene terephthalate, a copolymer consisting of polyethylene terephthalate and polyethylene isophthalate and a poly(1,4-cyclohexane dimethylene terephthalate).

16. An artificial blood vessel according to claim 14, wherein said aromatic polyester is a polyethylene glycol.

17. An artificial blood vessel according to claim 1, wherein said composite fibers have an elongation percentage of not less than 2% to be an elongation elastic recovery rate of 90%.

18. An artificial blood vessel according to claim 2, wherein said composite fibers have an elongation percentage of not less than 2% to be an elongation elastic recovery rate of 90%.

19. An artificial blood vessel according to claim 1, which further comprises a spiral or ring reinforcement made of a polyolefin resin for reinforcing said tubular body, said spiral or ring reinforcement extending along the outside periphery of said artificial blood vessel.

20. An artificial blood vessel according to claim 2, which further comprises a spiral or ring reinforcement made of a polyolefin resin for reinforcing said tubular body, said spiral or ring reinforcement extending along the outside periphery of said artificial blood vessel.

* * * * *

UNITED STATES PATENT AND TRADEMARK OFFICE
CERTIFICATE OF CORRECTION

PATENT NO. : 5,545,212
DATED : August 13, 1996
INVENTOR(S) : Sobei WAKABAYASHI et al It is certified that error appears in the above-indentified patent and that said Letters Patent is hereby corrected as shown below:

In Column 1, line 62, delete "Marched" and insert -- Matched --.
In Column 2, line 8, delete "Tahara" and insert -- Tabata --.
In Column 4, line 23, delete "Pelprene-S-type" and insert -- Pelprene-P-type --.
In Column 4, line 26, delete "polyester-polyester" and insert
-- polyester-polyether --.
In Column 5, line 42, delete "Structural" and insert -- structural --.
In Column 5, line 46, delete "antithrombogenisity" and insert
-- antithrombogenicity --.
In Column 6, line 59, delete "cc/min./cm$^2$-110 mmHg" and insert -- cc/min./cm$^2$-120 mmHg --.
In Column 7, lines 51, delete "form" and insert -- each forming --.

Signed and Sealed this

Twenty-second Day of October, 1996

*Attest:*

BRUCE LEHMAN

*Attesting Officer*     *Commissioner of Patents and Trademarks*